US006814574B2

United States Patent
Abolfathi et al.

(10) Patent No.: US 6,814,574 B2
(45) Date of Patent: Nov. 9, 2004

(54) DENTAL PLIERS FOR FORMING AND REMOVING BUMPS ON APPLIANCES

(75) Inventors: Amir Abolfathi, Menlo Park, CA (US); Brian K. Asselin, San Jose, CA (US); Eric Kuo, Foster City, CA (US); Loc X. Phan, San Jose, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

(21) Appl. No.: 10/289,551

(22) Filed: Nov. 6, 2002

(65) Prior Publication Data

US 2004/0086823 A1 May 6, 2004

(51) Int. Cl.[7] .................................................. A61C 3/00
(52) U.S. Cl. ............................................. 433/4; 433/159
(58) Field of Search ............................... 433/3, 4, 159, 433/157, 158, 6, 18; 140/121; 81/424.5, 426, 426.5

(56) References Cited

U.S. PATENT DOCUMENTS

| | | | |
|---|---|---|---|
| 634,493 A | 10/1899 | Bradley et al. | |
| 770,162 A | * 9/1904 | Chase | 433/156 |
| 1,304,720 A | 5/1919 | Young et al. | |
| 1,316,409 A | 9/1919 | Bahre et al. | |
| 3,727,316 A | 4/1973 | Goldberg et al. | |
| 3,911,583 A | 10/1975 | Hoffman et al. | |
| 4,070,745 A | 1/1978 | Schimmelman et al. | |
| 4,310,305 A | 1/1982 | Frajdenrajch et al. | |
| 4,414,868 A | * 11/1983 | Puro | 81/416 |
| 5,011,491 A | 4/1991 | Boenko et al. | |
| 5,084,935 A | 2/1992 | Kalthoff et al. | |
| 5,168,616 A | * 12/1992 | Klein | 29/268 |
| 5,197,879 A | * 3/1993 | Fowler et al. | 433/159 |
| 5,197,880 A | 3/1993 | Lovaas et al. | |
| 5,257,558 A | 11/1993 | Farzin-Nia et al. | |
| 5,395,236 A | 3/1995 | Khouri et al. | |
| 5,538,421 A | 7/1996 | Aspel et al. | |
| 5,588,832 A | 12/1996 | Farzin-Nia et al. | |
| 6,293,790 B1 | 9/2001 | Hilliard et al. | |

* cited by examiner

Primary Examiner—Kevin Shaver
Assistant Examiner—Melba Bumgarner
(74) Attorney, Agent, or Firm—Bao Q. Tran

(57) ABSTRACT

Pliers for forming and removing bumps for the dental appliance without heating are disclosed. The eraser pliers for erasing a bump on an appliance include a first elongated member having a first jaw portion at one end and a handle portion at the other end, the jaw portion having flat surface mounted at a distal end of the first jaw portion; and a second elongated member joined to the first elongated member, the second elongated member having a second jaw portion at one end and a second handle portion at the other end, the second jaw portion having a second flat surface mounted at a distal end of the second jaw portion, the first and second flat surfaces adapted to engage and flatten the bump. The pliers for making the bumps include a first elongated member having a first jaw portion at one end and a handle portion at the other end, the jaw portion having a projection mounted at a distal end of the first jaw portion; and a second elongated member joined to the first elongated member, the second elongated member having a second jaw portion at one end and a second handle portion at the other end, the second jaw portion adapted to receive the projection to create the bump in the dental appliance without heating.

18 Claims, 5 Drawing Sheets

DENTAL PLIERS FOR FORMING AND REMOVING BUMPS ON APPLIANCES

BACKGROUND

This invention relates in general to pliers for forming and removing bumps on dental repositioning appliances.

Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing what are commonly referred to as "braces." Braces comprise a variety of appliances such as brackets, bands, archwires, ligatures, and O-rings. After they are bonded to the teeth, periodic meetings with the orthodontist are required to adjust the braces. This involves installing different archwires having different force-inducing properties or by replacing or tightening existing ligatures. Between meetings, the patient may be required to wear supplementary appliances, such as elastic bands or headgear, to supply additional or extraoral forces.

Although conventional braces are effective, they are often a tedious and time consuming process requiring many visits to the orthodontist's office. Moreover, from a patient's perspective, they are unsightly and uncomfortable. Consequently, alternative orthodontic treatments have developed. A particularly promising approach relies on the use of elastic positioning appliances for realigning teeth. Such appliances comprise a thin shell of elastic material that generally conforms to a patient's teeth but is slightly out of alignment with the initial tooth configuration. Placement of the elastic positioner over the teeth applies controlled forces in specific locations to gradually move the teeth into the new configuration. Repetition of this process with successive appliances with new configurations eventually move the teeth through a series of intermediate configurations to a final desired configuration. A full description of an exemplary elastic polymeric positioning appliance is described in U.S. Pat. No. 5,975,893, and in published PCT application WO 98/58596 which designates the United States and which is assigned to the assignee of the present invention. Both documents are incorporated by reference for all purposes.

In addition to their ease of use, polymeric positioning appliances are generally transparent, providing an improved cosmetic appearance, and impart substantial force on the teeth, due to stiffness of the appliance. The stiffness of an elastic positioning appliance is a result of the modulus of the polymer materials from which it is made. The higher the modulus of the materials, the higher the stiffness of the appliance. When a patient positions such an appliance over a prescribed group of teeth, one or more of the teeth will provide a base or anchor region for holding the positioning appliance in place while the stiffness of the polymeric material will impart a resilient repositioning force against one or a portion of the remaining teeth. However, the stiffer the appliance, the more difficult it is to slip the misaligned appliance over the teeth and fully engage the appropriate surfaces; the appliance often has the tendency to disengage or "pop off". Likewise, once it is firmly seated, it is more difficult to remove. Further, a stiff appliance is less forgiving in cases of lowered patient compliance. If a patient were to remove the appliance for an unprescribed period of treatment time, the patient's teeth may move slightly out of the planned tooth arrangement. When attempting to reapply the appliance, it may be too rigid to accommodate these slight differences and a new appliance may need to be created. Similarly, the tooth positions defined by the cavities in each successive appliance must not differ beyond a limiting dimension from those defined by the prior appliance or, again, it may be too rigid to accommodate the differences. Consequently, only small increments in tooth repositioning may be made with each appliance.

During application of the appliance, it is useful to form bumps in a polymeric appliance to facilitate minor orthodontic movements. The bumps apply corrective pressure to a patient's teeth allowing the doctor to optimize the adaptation of the appliance to the teeth. One method of forming these bumps is by using a heated rod that works like a soldering iron to form a cylindrical bump in the appliance. The soldering iron must be heated electrically and works effectively only on specific polymeric materials, rather than on all polymeric materials.

U.S. Pat. No. 6,293,790 to Hilliard entitled "Heated orthodontic pliers" relates to an assortment of orthodontic pliers that are capable of forming different shaped ramps, imprinted logos, logo pockets, fluoride and bleach pockets, bite plates, rectangular shapes for retention of blocks on any polymeric appliance and pinching down on loose fasteners when heated to a sufficient temperature. This will allow orthodontists to make the minor modifications that are often necessary in a cost effective manner. The Hilliard patent specifically noted that "[no] patent discloses the necessity to heat the dental pliers for forming bumps or pinching loosely held fasteners in the polymeric appliance."

SUMMARY

A system to form and erase bumps on a dental appliance without heating is disclosed. In one aspect, dental pliers to create a bump in a dental appliance without requiring heating include a first elongated member having a first jaw portion at one end and a handle portion at the other end, the jaw portion having a projection mounted at a distal end of the first jaw portion; and a second elongated member joined to the first elongated member, the second elongated member having a second jaw portion at one end and a second handle portion at the other end, the second jaw portion adapted to receive the projection to create the bump in the dental appliance without heating.

In another aspect, eraser pliers for erasing the bump include a first elongated member having a first jaw portion at one end and a handle portion at the other end, the jaw portion having flat surface mounted at a distal end of the first jaw portion; and a second elongated member joined to the first elongated member, the second elongated member having a second jaw portion at one end and a second handle portion at the other end, the second jaw portion having a second flat surface mounted at a distal end of the second jaw portion, the first and second flat surfaces adapted to engage and flatten the bump.

Implementations of the above aspect may include one or more of the following. The second handle is pivotally joined to the first handle. The appliances can be made from a polymeric material such as a hard block polyurethane polymer such as IsoplastTm manufacture by Dow Chemical, TecoplastTm manufacture by Thermadics Polymer Products, polyester polycarbonate blends and polycarbonate such as XylexTm and LexanTm respectively manufacture by GE Corporation, and polyester homopolymer such as EastarTm manufacture by Eastman Chemical. The material may be from the classes of polymers given above as examples but not limited to those alone. The material may be homopolymer, heteropolymer, polymer blends, coextruded polymer with each layer being a different material or the same material and may be in different thicknesses. The material may also be a thermalset or any suitable material capable of elongation in accordance with the design and dimensions dictated by the pliers' tips without causing puncture.

In another aspect, dental pliers for erasing a bump formed on a dental appliance, includes a first handle having a first tip with a flat surface positioned thereon; and a second handle pivotally joined to the first handle, the second handle having a tip with a flat surface adapted to engage the first flat surface to flatten a projection at room temperature.

Advantages of the invention may include one or more of the following. The pliers can be used for either forming or removing bumps or pressure points on orthodontic polymeric appliances. Bumps may be formed on the appliance surface resulting in orthodontic pressure that allows for the minor repositioning of teeth. The ability to fabricate bumps provides the doctor with increased flexibility and options during treatment. The bumps may be used to accomplish minor anterior rotations, minor anterior in-out tooth movement, tightening light interproximal contacts and enhancing appliance retention in undercut regions. The pliers are designed to allow for the fabrication of bumps without heating any part of the pliers jaw. This is achieved by designing the jaw tips to allow the polymeric to be stretched at ambient conditions.

DESCRIPTION

The present invention provides improved devices, systems and methods for incrementally repositioning teeth using a plurality of discrete polymeric appliances of variable flexibility, where each appliance successively repositions one or more of the patient's teeth by relatively small amounts. Flexibility may be enhanced by applying the pliers to form bump(s) on the polymeric material. The bumps may vary within a given appliance or may vary throughout a series of appliances according to a prescribed orthodontic treatment plan.

According to the present invention, systems and methods are provided for incrementally moving teeth using a plurality of discrete appliances, where each appliance successively moves one or more of the patient's teeth by relatively small amounts. The tooth movements will be those normally associated with orthodontic treatment, including translation in all three orthogonal directions relative to a vertical centerline, rotation of the tooth centerline in the two orthodontic directions ("root angulation" and "torque"), as well as rotation about the centerline.

Figure 1A:
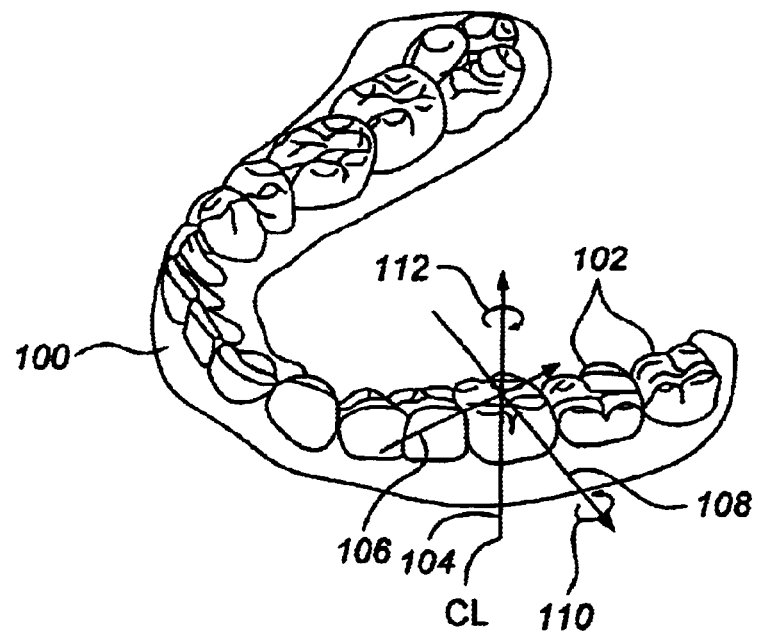
FIG. 1A illustrates a patient's jaw and provides a general indication of how teeth may be moved by the methods and apparatus of the present invention.
Figure 1B:
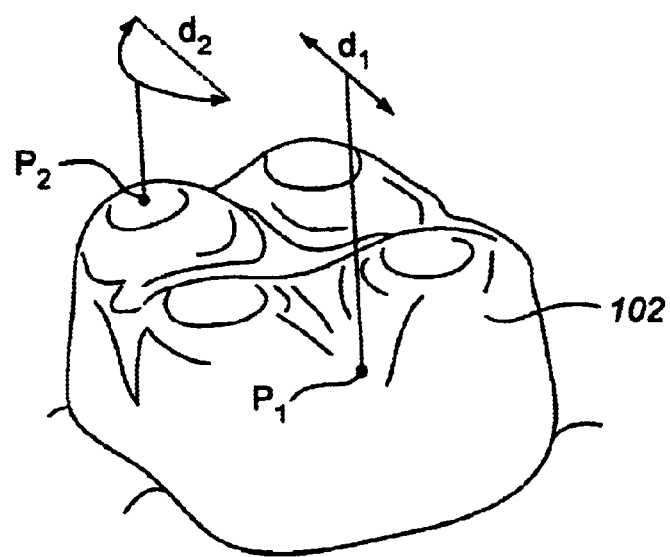
FIG. 1B illustrates a single tooth from FIG. 1A and defines how tooth movement distances are determined.

Referring now to FIG. 1A, a representative jaw 100 includes sixteen teeth 102. The present invention is intended to move at least some of these teeth from an initial tooth arrangement to a final tooth arrangement. To understand how the teeth may be moved, an arbitrary centerline (CL) is drawn through one of the teeth 102. With reference to this centerline (CL), the teeth may be moved in the orthogonal directions represented by axes 104, 106, and 108 (where 104 is the centerline). The centerline may be rotated about the axis 108 (root angulation) and 104 (torque) as indicated by arrows 110 and 112, respectively. Additionally, the tooth may be rotated about the centerline, as represented by arrow 104. Thus, all possible free-form motions of the tooth can be performed. Referring now to FIG. 1B, the magnitude of any tooth movement achieved by the methods and devices of the present invention will be defined in terms of the maximum linear translation of any point $P_i$ on a tooth 102. Each point $P_i$ will undergo a cumulative translation as that tooth is moved in any of the orthogonal or rotational directions defined in FIG. 1A. That is, while the point will usually follow a non-linear path, there will be a linear distance between any point in the tooth when determined at any two times during the treatment. Thus, an arbitrary point $P_1$ may in fact undergo a true side-to-side translation as indicated by arrow $d_1$, while a second arbitrary point $P_2$ may travel along an arcuate path, resulting in a final translation $d_2$. Many aspects of the present invention are defined in terms of the maximum permissible movement of a point $P_i$ induced by the methods in any particular tooth. Such maximum tooth movement, in turn, is defined as the maximum linear translation of that point $P_i$ on the tooth which undergoes the maximum movement for that tooth in any treatment step.

Figure 1C:
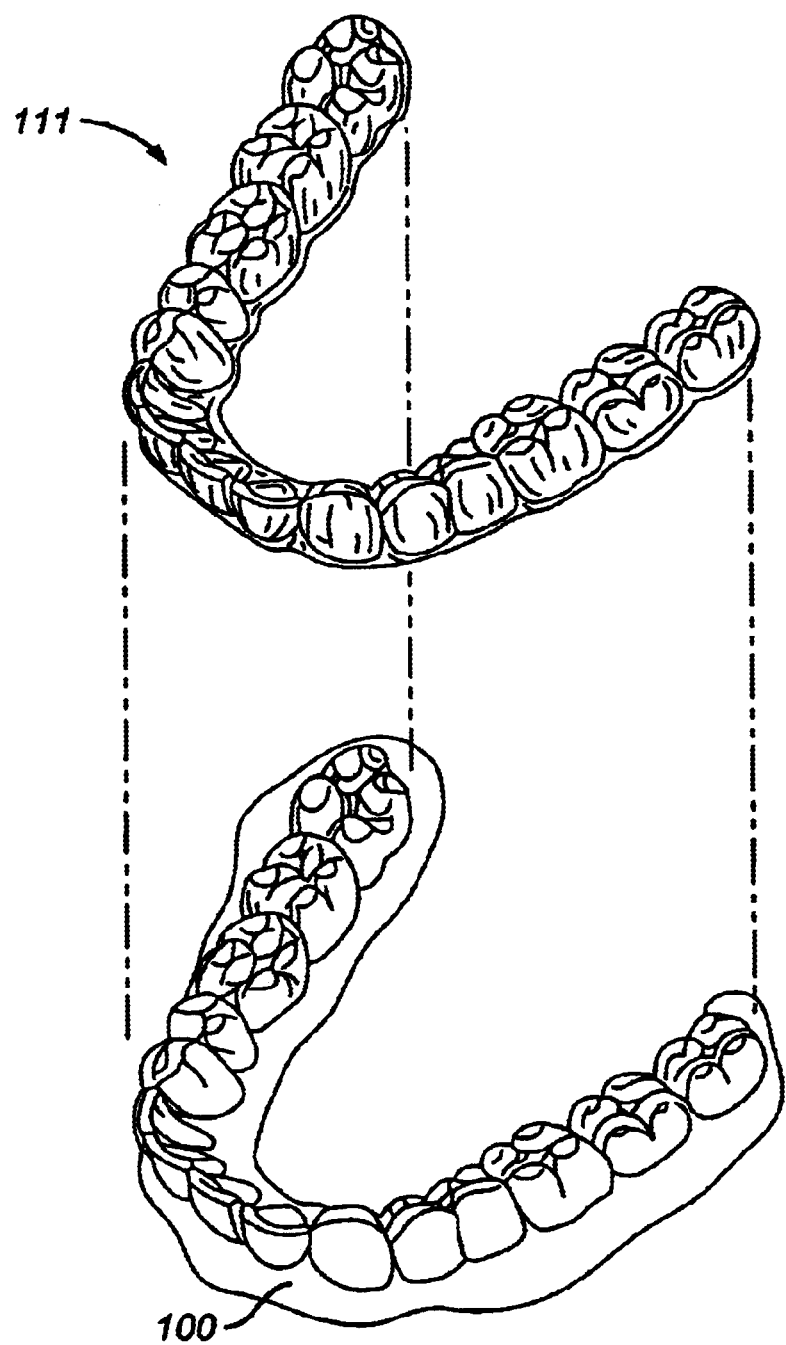
FIG. 1C illustrates the jaw of FIG. 1A together with an incremental position adjustment appliance which has been configured according to the methods of the present invention.

Referring now to FIG. 1C, systems according to the present invention include a plurality of incremental position adjustment appliances. The appliances are intended to effect incremental repositioning of individual teeth in the jaw as described generally above. In a broadest sense, the methods of the present invention can employ any of the known positioners, retainers, or other removable appliances which are known for finishing and maintaining teeth positions in connection with conventional orthodontic treatment. The systems of the present invention, in contrast with prior apparatus and systems, will provide a plurality of such appliances intended to be worn by a patient successively in order to achieve the gradual tooth repositioning as described herein. A preferred appliance 111 will comprise a polymeric shell having a cavity shaped to receive and resiliently reposition teeth from one tooth arrangement to a successive tooth arrangement. The polymeric shell will preferably, but not necessarily, fit over all teeth present in the upper or lower jaw. Often, only certain one(s) of the teeth will be repositioned while others of the teeth will provide a base or anchor region for holding the repositioning appliance in place as it applies the resilient repositioning force against the tooth or teeth to be repositioned in complex cases, however, many or most of the teeth will be repositioned at some point during the treatment. In such cases, the teeth which are moved can also serve as a base or anchor region for holding the repositioning appliance. Additionally, the gums and/or the palette can serve as an anchor region, thus allowing all or nearly all of the teeth to be repositioned simultaneously.

The polymeric appliance 111 of FIG. 1C is preferably formed from a thin sheet of a suitable elastomeric polymer such as hard block polyurethane polymer such as Isoplast™ manufacture by Dow Chemical, Tecoplast™ manufacture by Thermadics Polymer Products, polyester polycarbonate blends and polycarbonate such as Xylex™ and Lexan™ respectively manufacture by GE Corporation, and polyester homopolymer such as Eastar™ manufacture by Eastman Chemical. The material may be from the classes of polymers given above as examples but not limited to those alone. The material may be homopolymer, heteropolymer, polymer blends, coextruded polymer with each layer being a different material or the same material and may be in different thicknesses. The material may also be a thermalset. The key component is that material has the ultimate elongation suitable to from the bumps to specific design and dimensions dictated by the pliers tip without causing puncture.

Usually, no wires or other means will be provided for holding the appliance in place over the teeth. In some cases, however, it will be desirable or necessary to provide individual anchors on tee with corresponding receptacles or apertures in the appliance 111 so that the appliance can apply an upward force on the tooth which would not be possible in the absence of such an anchor. Specific methods for producing the appliances 111 are described hereinafter.

Figure 2A:
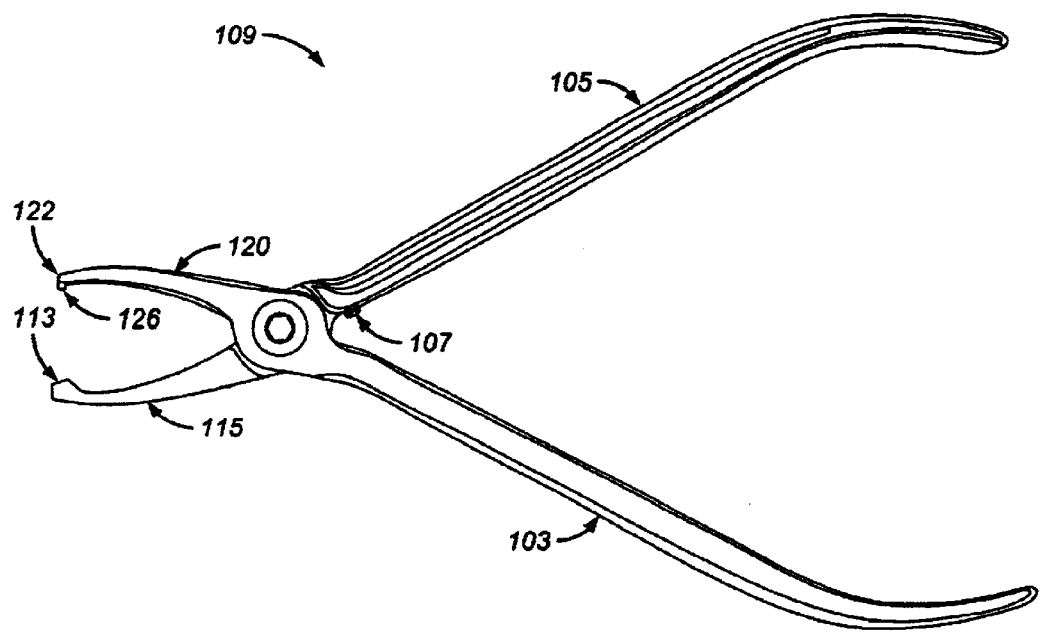
FIGS. 2A and 2B illustrate an exemplary embodiment of dental pliers for forming bumps onto the appliance of FIGS. 1A–1C.
Figure 2B:
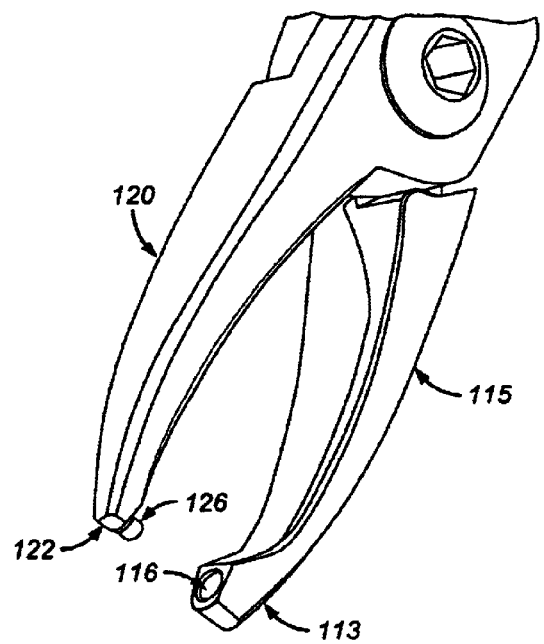

FIGS. 2A and 2B illustrate an exemplary embodiment of dental pliers for forming bumps onto a dental appliance, such of that of FIG. 1C. The dental pliers 109 have handles 103 and 105. The handle 103 has a jaw 115. The jaw 115 is curved and has a tip 113. A flat surface is provided at the distal end. The tip 113 has a throughbore at 116 (FIG. 2B). In one embodiment, the throughbore is cylindrical in shape. However, other suitable shapes can be provided therein.

Correspondingly, the handle 105 has a jaw 120. The jaw 120 has a tip 122. At or near the end of the tip 122 is a projection 126. The projection 126 is cylindrical in shape and in one embodiment is adapted to be received by throughbore 116. The pliers 109 also have a set screw 107 for adjusting the clearance between the cylindrical projection and the throughbore. The 107 screw can be adjusted using an alien wrench in one embodiment.

The pliers consist of a pair of handles each with a curved jaw member lying in the same plane as the handle. The handles are subapically and pivotally connected. A dome shaped cylindrical bump forming projection is positioned at the tip of the first jaw. A circular shaped throughbore is situated in the tip of the second jaw. The second jaw is typically longer than the first jaw by about ½ to 2 millimeters, preferably between 0.6 to 1 millimeter. The pliers are preferably manufactured from stainless steel and are able to withstand sterilization, i.e., an autoclave or high heat.

To form a bump the appliance is first positioned between the open jaw tips. As the handles are closed the cylindrical bump forming projection produces a force vector normal to the polymeric surface causing it to expand and stretch into the circular shaped throughbore. The bump height may be easily adjusted by drilling a hole in the handle near the pivot point and inserting a set screw 107. By turning the set screw in or out the user may adjust the clearance of the bump forming projection in the throughbore thereby varying the bump height. Before making bumps on an appliance the user may "calibrate" the bump size by forming bumps on a flat sheet of the polymeric material.

Typically the bump forming projection is a cylinder with a domed/curved top side. The projection height may vary and is a function of the polymeric elasticity. Typically the bump height is between 0.5 mm–2.0 mm and more preferably between 1.00 mm and 1.5 mm. Bumps are typically formed on either the retainer buccal or lingual surface so that the bump apex is facing towards the tooth.

Occasionally a bump may be fabricated in the wrong position and it may be necessary to remove it. Consequently there is a need for a simple tool that efficiently removes unwanted bumps from appliance surfaces. The pliers are fabricated from two substantially identical halves; the jaw tips are machined to form an inwardly facing flat surface. Alternatively one of the inward facing surfaces may be slightly convex with the other surface slightly concave. When using the pliers, the jaw tip is positioned over the bump and the handles are squeezed resulting in force that flattens of the bump.

Although the elastic positioner appliances generate controlled forces resulting in tooth movement occasionally these forces do not always result in a tooth moving completely into its final desired position. In this situation the pliers would be used by the doctor to form a bump in a position on the appliance protruding towards the tooth to be moved that causes an additional force moving the tooth into its final desired position. It is not necessary to modify the appliance in any fashion since the space is already built into the appliance for the tooth to move into. Therefore, the bump is applied for minor tooth movements anywhere from ½ mm to about 1.5 mm and there are a number of tooth movements that may be accomplished, such as rotation and torqueing being examples of two movements. Multiple bumps may be placed inside of any given appliance and repositioned as needed. The pliers may be used either during the course of treatment or at the end of treatment to accomplish minor fine-tuning that is not accomplished by the appliance during the course of treatment to accomplish minor tooth movements.

The bump when formed always comes in contact with the desired tooth that must be moved. The bump height is limited by the stretchability of the thermal plastic at room temperature. The uniqueness of this invention in accomplishing the fabrication of the bumps at room temperature based on the design of the cylindrical bump projection and the size of the throughbore which allows for the stretching of the thermal plastic at room temperature.

A bump that is made on a wrong surface or improper surface may be eliminated through the use of the eraser appliances. The doctor can calibrate making bumps using a thermal plastic sheet of material and practice making bumps prior to making the actual bumps on an appliance, calibrating the height of the bump before making it on the appliance.

This device allows the doctor to fabricate bumps on a dental appliance without heating the pliers. Definition of room temperature would be any temperature between freezing and 104 degrees which, as defined by the USP, is between 15–30 C.

Figure 3:
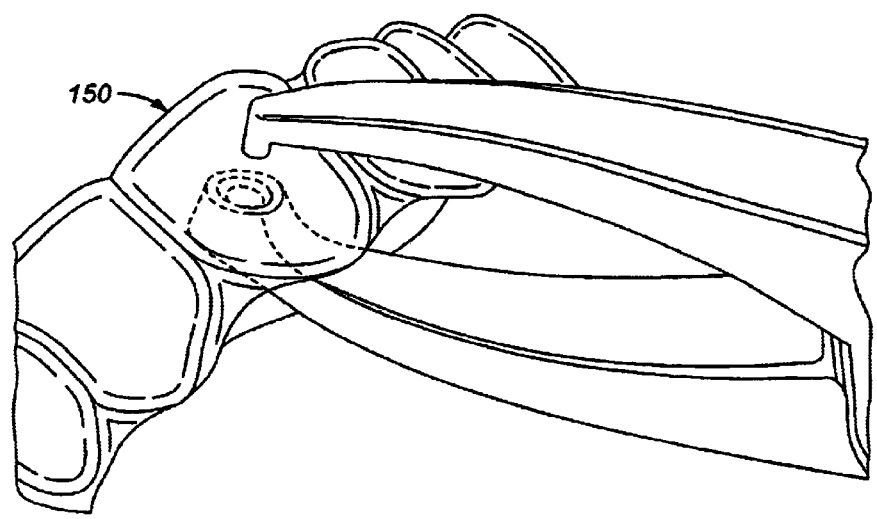
FIG. 3 shows an exemplary application of the pliers of FIGS. 2A and 2B onto a dental appliance.
Figure 4A:
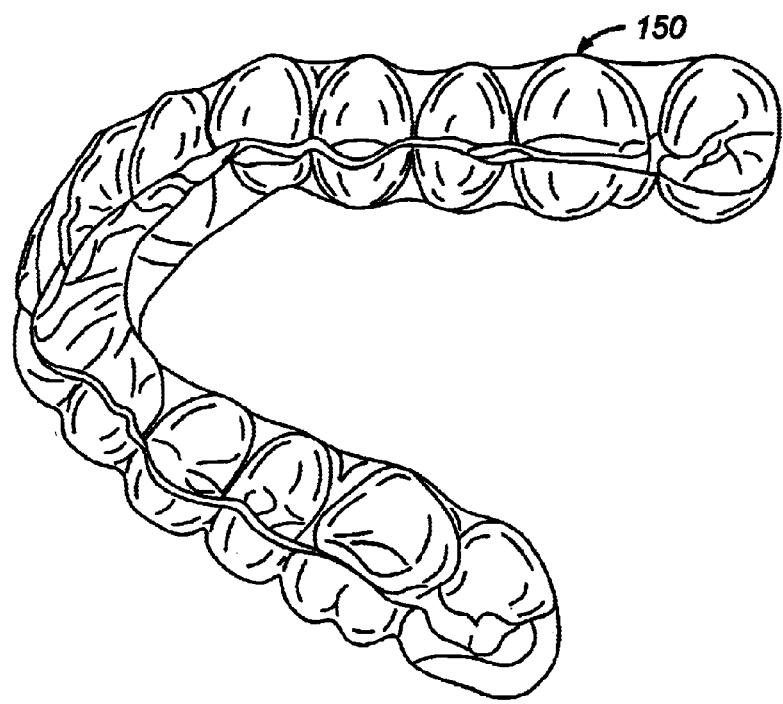
FIGS. 4A and 4B illustrate a bump formed on a dental appliance before application of the dental pliers and after the application of the pliers.
Figure 4B:
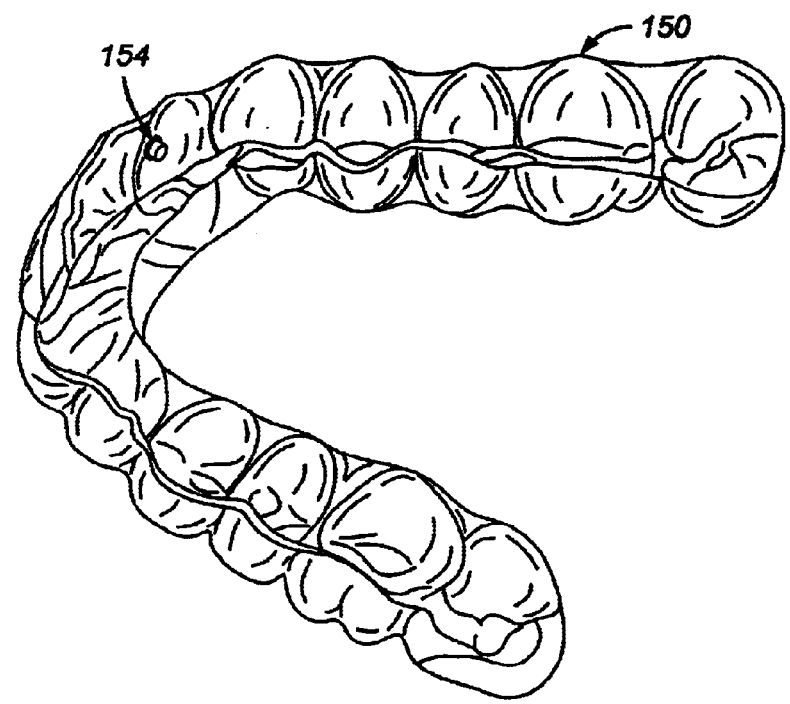

FIG. 3 shows an exemplary application of the pliers of FIGS. 2A and 2B onto a dental appliance, while FIGS. 4A and 4B illustrate an original dental appliance before application of the dental pliers of FIGS. 2A and 2B and after the application of the pliers respectively.

In FIG. 4A, the appliance 150 has a portion in which a dental practitioner wishes to form a bump or projection toward the patient's tooth when worn. FIG. 4B illustrates the appliance 150 with and a bump or a projection 154 formed through the application of the pliers 109.

Figure 5:
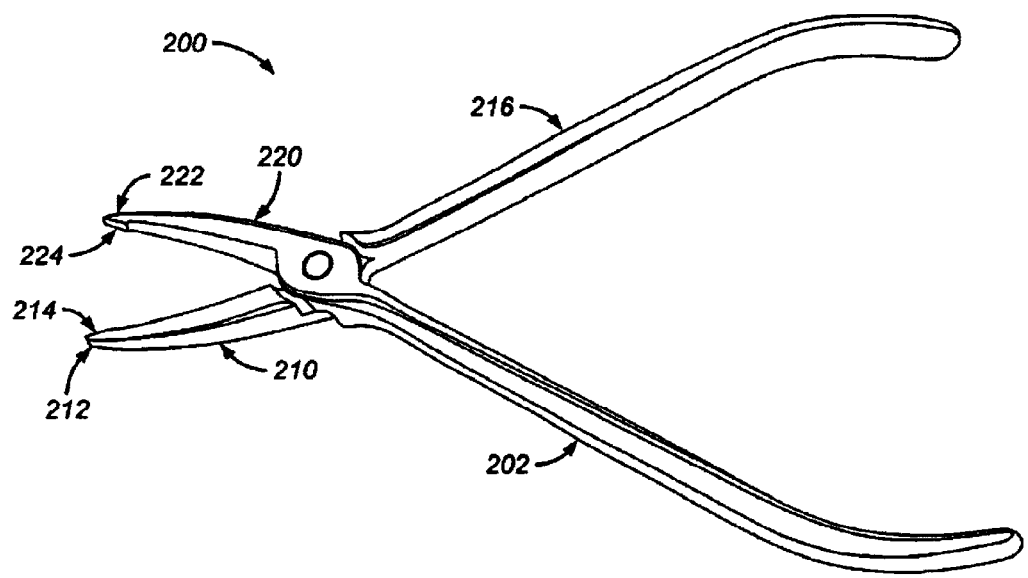
FIG. 5 illustrates an exemplary embodiment of dental pliers for removing bumps from the appliance.

On occasion, a practitioner may have formed a bump that was unnecessary. In this case, eraser pliers can be used. FIG. 5 illustrates exemplary eraser dental pliers 200. Similar to the pliers 109 of FIGS. 2A and 2B, the pliers 200 include a handle 202 having a lower jaw 210. The lower jaw 210 form has a tip 212 at a distal end. On top of the tip 212 is a flat surface 214. Correspondingly, a handle 216 includes a jaw of 220 with a tip 222 and a corresponding flat surface 224. The flat surfaces 214 and 224 cooperate such that when applied to a bump on a dental appliance, the flat surfaces 214 and 224 press the material from a bump back into a flat surface for undoing a bump.

For training purposes, a plurality of sheets of thermal plastic forming material can be provided for the practitioner to apply (and calibrate) the dental pliers 109 and the eraser pliers 200. The calibration sheet allows doctors to establish the depth of the bumps that are to be made by the pliers prior to the application of the pliers on the actual dental appliances.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow. For example, bumps have been mentioned as a specific application of the pliers. However, any suitable impression or projection or deformation may be created by the appliances of the invention. Whereas particular embodiments of the present invention have been described herein for purposes of illustration, it will be evident to those skilled in the art that numerous variations of the details may be made without departing from the invention as defined in the appended claims.

What is claimed is:

1. Dental system, comprising:
 a dental appliance including a polymeric shell having a cavity shaped to receive and resiliently reposition teeth; and
 a bump-forming pliers, including:
  a first elongated member having a first jaw portion at one end and a first handle portion at the other end, the jaw portion having a projection mounted at a distal end of the first jaw portion; and
  a second elongated member joined to the first elongated member, the second elongated member having a second jaw portion at one end and a second handle portion at the other end, the second jaw portion adapted to receive the projection to create the bump in the dental appliance without heating.

2. The system of claim 1, wherein a bump is formed at room temperature.

3. The system of claim 1, wherein the second handle portion is pivoxally joined to the first handle portion.

4. The system of claim 1, wherein the dental appliance comprises an elastomeric polymer.

5. The system of claim 1, wherein the polymeric shell comprises one of the following: hard block polyurethane polymer, polyester polycarbonate blends, polycarbonate, and polyester homopolymer.

6. A system to create a bump without requiring heating, comprising:
 a dental appliance including a polymeric shell having a cavity shaped to receive and resiliently reposition teeth;
 a bump-forming pliers, including:
  a first elongated member having a first jaw portion at one end and a first handle portion at the other end, the jaw portion having a projection mounted at a distal end of the first jaw portion; and
  a second elongated member joined to the first elongated member, the second elongated member having a second jaw portion at one end and a second handle portion at the other end, the second jaw portion adapted to receive the projection to create the bump in the dental appliance without healing; and
 eraser pliers for flattening the created bump, including:
  a first elongated member having a first-jaw portion at one end and a first handle portion at the other end, the jaw portion having a first flat surface mounted at a distal end of the first jaw portion; and
  a second elongated member joined to the first elongated member, the second elongated member having a second jaw portion at one end and a second handle portion a; the other end, the second jaw portion having a second flat surface mounted at a distal end of the second jaw portion, the first and second flat surfaces adapted to engage and flatten the bump.

7. The system of claim 6, wherein a bump is formed in the dental appliance at room temperature.

8. The system of claim 6, wherein each of the second handle portion is pivotally joined to each of the first handle portion.

9. The system of claim 6, wherein the appliance comprises an elastomeric polymer.

10. The system of claim 6, wherein the polymeric shell comprises one of the following: hard block polyurethane polymer, polyester polycarbonate blends, polycarbonate, and polyester homopolymer.

11. Eraser system, comprising:
 a dental appliance comprising a polymeric shell having a cavity shaped to receive and resiliently reposition teeth, the appliance having a bump thereon; an eraser pliers including:
 a first elongated member having a first jaw portion at one end and a handle portion at the other end, the jaw portion having a first flat surface mounted at a distal end of the first jaw portion; and
 a second elongated member joined to the first elongated member, the second elongated member having a second jaw portion at one end and a second handle portion at the other end, the second jaw portion having a second flat surface mounted at a distal end of the second jaw portion, the first and second flat surfaces adapted to engage and flatten the bump.

12. The system of claim 11, wherein a flattened bump in the dental appliance is flattened at room temperature.

13. The system of claim 11, wherein the second handle portion is pivotally joined to the first handle portion.

14. The system of claim 11, wherein the appliance comprises an elastomeric polymer.

15. The system of claim 11, wherein the polymeric shell comprises one of the following homopolymer, heteropolymer, polymer blends, coextruded polymer with each layer being a different material or the same material, and thermalset.

16. Dental system comprising:
 a dental appliance comprising a polymeric shell having a cavity shaped to receive-and-resiliently reposition teeth, the appliance having a bump formed thereon;
 an eraser pliers including:
  a first handle having a first tip with a flat surface positioned thereon; and
  a second handle pivotally joined to the first handle, the second handle having a tip with a flat surface adapted to engage the first flat surface to flatten the bump at room temperature.

17. The system of claim 16, wherein the dental appliance comprises a polymeric material selected from one of the following: hard block polyurethane polymer, polyester polycarbonate blends, polycarbonate, and polyester homopolymer.

18. The system of claim 16, wherein the dental appliance comprises a polymeric material selected from one of the following: homopolymer, heteropolymer, polymer blends, coextruded polymer, and thermalset.

* * * * *